(12) United States Patent
Renzi et al.

(10) Patent No.: US 6,686,401 B1
(45) Date of Patent: Feb. 3, 2004

(54) LIQUID COMPOSITION POLYMERIZABLE INTO ORGANIC GLASS HAVING GOOD OPTICAL AND PHYSICO-MECHANICAL PROPERTIES

(75) Inventors: Fiorenzo Renzi, Cervia-Ravenna (IT); Andrea Bendandi, Ravenna (IT); Roberto Forestieri, Ravenna (IT)

(73) Assignee: Great Lakes Chemical (Europe) GmbH, Frauenfeld (CH)

( * ) Notice: Subject to any disclaimer, the term of this patent is extended or adjusted under 35 U.S.C. 154(b) by 64 days.

(21) Appl. No.: 10/069,600

(22) PCT Filed: Aug. 23, 2000

(86) PCT No.: PCT/EP00/08264
§ 371 (c)(1),
(2), (4) Date: May 16, 2002

(87) PCT Pub. No.: WO01/16194
PCT Pub. Date: Mar. 8, 2001

(30) Foreign Application Priority Data

Aug. 31, 1999 (IT) .......................... MI99A1850

(51) Int. Cl.$^7$ ................................. C08F 2/46
(52) U.S. Cl. ................ 522/179; 528/272; 528/275; 528/300; 528/301; 528/302; 528/306; 528/307; 528/308; 528/308.6; 522/24; 522/60; 522/101; 522/104; 522/165; 524/81; 524/115; 524/126; 524/128; 524/186

(58) Field of Search ................. 528/272, 275, 528/300, 301, 302, 306, 307, 308, 308.6; 522/24, 60, 101, 104, 165, 179; 524/115, 81, 126, 128, 186

(56) References Cited

U.S. PATENT DOCUMENTS

| 4,508,656 A | * | 4/1985 | Romano et al. | ............ 558/265 |
| 4,602,075 A | | 7/1986 | Kida et al. | |
| 4,623,705 A | * | 11/1986 | Romano et al. | ............... 526/75 |

FOREIGN PATENT DOCUMENTS

| EP | 0 284 139 | 9/1988 |
| JP | 59 045312 | 3/1984 |
| JP | 60 012503 | 1/1985 |
| JP | 06 175081 | 9/1994 |

* cited by examiner

*Primary Examiner*—Samuel A. Acquah
(74) *Attorney, Agent, or Firm*—Oblon, Spivak, McClelland, Maier & Neustadt, P.C.

(57) ABSTRACT

Liquid composition polymerizable, by means of radicalic polymerization, into organic glass, comprising the product obtained from the transesterification of a mixture of diallyl carbonate (A) and a phthalic ester (B), with one or more polyols (C), linear or branced, containing from two to eight carbon atoms in the molecule.

28 Claims, No Drawings

LIQUID COMPOSITION POLYMERIZABLE INTO ORGANIC GLASS HAVING GOOD OPTICAL AND PHYSICO-MECHANICAL PROPERTIES

The present invention relates to a liquid composition polymerizable into organic glass.

More specifically, the present invention relates to a liquid composition which can be polymerized, by means of radicalic polymerization, into organic glass with a refractive index $(n_D^{20}) \geq 1.53$, having good optical and physico-mechanical properties, and good dyeability, comprising the product obtained from the transesterification of a mixture of diallyl carbonate (A) and a phthalic ester (B), with one or more polyols (C), linear or branched, containing from two to eight carbon atoms in the molecule, a process for its preparation and its use in the preparation of organic glass.

A further object of the present invention relates to the organic glass obtained from the polymerization of said composition and the end-products obtained starting from said composition such as, for example, ophthalmic lenses and lenses for optical instruments.

Organic glass obtained from the polymerization of bis (allyl carbonate of diethylene glycol has been known and used for many years in this specific field. The use of the above organic glass, however, in the preparation of optical articles such as, for example, ophthalmic lenses, has various disadvantages mainly due to their relatively low refractive index $(n_D^{20})$ in the order of 1.50.

As a result of this, especially in the case of high power ophthalmic lenses, these lenses have poorer aesthetic characteristics owing to the greater thickness and also lose the advantages of lightness due to the limited specific weight.

In order to overcome these drawbacks, compositions polymerizable into organic glass having a higher refractive index, have been prepared in the known art.

To achieve this objective, resort has been made to the introduction, in the above compositions, of reactive monomers or comonomers containing aromatic groups: among these, those consisting of allyl esters of aromatic carboxylic acids such as, for example, diallyl orthophthalate, diallyl isophthalate, diallyl terephthalate, triallyl trimellitate, etc., are of particular interest.

The introduction of the above species allows the refractive index $(n_D^{20})$ to be increased up to values ranging from 1.53 to 1.57 and gives the optical articles produced good mechanical properties and thermal resistance.

Polymerizable compositions of the above type are described, for example, in European patent applications: EP 371,140, EP 392,514, EP 472,161 and EP 305,048.

Optionally, the diallylphthalate is added to the above compositions in the form of "diallylphthalate component" which consists of the product obtained from the reaction between diallyl phthalate and a glycol as described, for example, in the following European patent applications: EP 540,003 and EP 540,043.

In the above European patent applications, bis(allyl carbonate) of diethylene glycol is indicated as second component of the polymerizable compositions. These compositions are polymerized into organic glass having a refractive index $(n_D^{20})$ equal to or higher than 1.53 using organic peroxides as polymerization initiators. The optic glass thus obtained has higher transparency characteristics, mechanical resistance to solvents, etc.

It has various disadvantages, however, linked to the fact that the components of the above polymerizable compositions have different reactivity and chemical characteristics. This makes it more difficult to control the polymerization reaction and results in the production of a polymeric end-product (for example, lenses) having a composition and properties which are not homogeneously distributed in the mass. This is demonstrated by the fact that the lenses obtained from the polymerization of said compositions, when observed in polarized light, have tensioned zones which can jeopardize their dimensional stability or create problems in the assembly phase of glasses.

The main problems, however, arise in the coloring operations of the above lenses, by immerging them in color baths using the known "dip dyeing" technique. In fact, the colored lenses thus obtained do not have uniform coloring due to the presence of areas with differing intensities. As color uniformity is one of the basic parameters which an optical article, such as an ophthalmic lens, must guarantee, the above problem is particularly serious.

The Applicant has now found that it is possible to overcome the above drawbacks of the known art by using a polymerizable liquid composition comprising mixed oligomers of allyl esters of aromatic carboxylic acids and aliphatic allyl carbonates, polymerized in the presence of organic polymerization initiators.

In particular, the Applicant has surprisingly found that the polymerizable liquid compositions object of the present invention, can be advantageously used for the preparation of organic glass having a refractive index $(n_D^{20}) \geq 1.53$, an excellent combination of optical and physico-mechanical properties and good dyeability by immersion in color baths.

An object of the present invention therefore relates to a liquid composition polymerizable, by means of radicalic polymerization, into organic glass, comprising the product obtained from the transesterification of a mixture of diallyl carbonate (A) and a phthalic ester (B), with one or more polyols (C), linear or branched, containing from two to eight carbon atoms in the molecule.

In the liquid composition object of the present invention, the molar ratio (A+B)/C ranges from 2/1 to 7/1 and the molar concentration of (B) in the mixture (A+B) ranges from 10% to 70% with respect to the total of said mixture (A+B).

In the polymerizable liquid composition object of the present invention, the molar ratio (A+B)/C preferably ranges from 2.5/1 to 5/1 and the molar concentration of (B) in the mixture (A+B) ranges from 20% to 60% with respect to the total of said mixture (A+B).

Phthalic esters (B) which can be used for the purposes of the present invention, are ortho, meta or paraphthalates of aliphatic alcohols containing from 1 to 3 carbon atoms in the molecule.

Specific examples of phthalic esters (B) useful for the purposes of the present invention are: dimethyl orthophthalate, dimethyl isophthalate, dimethyl terephthalate, diethyl orthophthalate, diethyl isophthalate, diethyl terephthalate, dipropyl orthophthalate, dipropyl isophthalate, dipropyl terephthalate, diallyl orthophthalate, diallyl isophthalate, diallyl terephthalate, etc.

Preferred phthalic esters for the purposes of the present invention are: dimethyl isophthalate, dimethyl terephthalate, diallyl isophthalate and diallyl terephthalate.

When a phthalic ester different from diallyl orthophthalate, diallyl isophthalate or diallyl terephthalate is used as component (B), allyl alcohol (D) must be added to the reaction mixture in a molar quantity equal to about 1–3 times that of the phthalate (B) to ensure that the reaction product exclusively consists of species having chain-end allyl functionalities.

Polyols (C) which can be used for the purposes of the present invention are polyols consisting of linear or branched aliphatic glycols, containing from two to eight carbon atoms in the molecule.

Specific examples of glycols useful for the purposes of the present invention are: ethylene glycol, diethylene glycol, triethylene glycol, tetra-ethylene glycol, 1,4-butanediol, 1,6-hexanediol, 1,3-propanediol, neopentylglycol, dipropyleneglycol, 2,2,4-trimethyl-1,3-pentanediol, etc.

Diethylene glycol is the preferred glycol for the purposes of the present invention.

Polyols (C) which can be used for the purposes of the present invention are also linear or branched aliphatic polyols containing from four to twenty carbon atoms and from three to six hydroxyl groups in the molecule.

Specific examples of polyols (C) containing from four to twenty carbon atoms and from three to six hydroxyl groups in the molecule useful for the purposes of the present invention are: pentaerythritol, trimethylolpropane, dipentaerythritol, ditrimethylolpropane, tris(hydroxyethyl) isocyanurate, etc.

Preferred polyols (C) containing from four to twenty carbon atoms and from three to six hydroxyl groups in the molecule for the purposes of the present invention are: pentaerythritol and trimethylolpropane.

For the purposes of the present invention, said polyols (C) containing from four to twenty carbon atoms and from three to six hydroxyl groups in the molecule, can only be used in the reaction mixture as a combination with the glycols described above in a concentration not exceeding 20% by weight with respect to the total weight of the mixture of polyols (C). Concentrations higher than 20%, in fact, cause an excessive increase in the viscosity of the polymerizable liquid composition and a deterioration in some of the properties of the end-products obtained from their processing, mainly their impact strength.

The polymerizable liquid composition object of the present invention is obtained starting from the mixture of diallyl carbonate (A), phthalic ester (B), polyol (C), and optionally, allyl alcohol (D), operating under transesterification conditions. More specifically, the reagents are put in contact with each other, in the proportions indicated above, and reacted at a temperature ranging from 80° C. to 160° C., preferably from 90° C. to 130° C., in the presence of a catalyst of the alkaline type, the low-boiling products which are formed as reaction by-product, being continually eliminated.

Catalysts of the alkaline type which can be used for the purposes of the present invention are: hydroxides, carbonates and alcoholates of alkaline metals, organic bases, basic ionic exchange resins.

Specific examples of catalysts of the alkaline type useful for the purposes of the present invention are: sodium hydroxide, sodium carbonate, sodium methylate.

The catalyst is conveniently used in a quantity equal to at least 1 ppm (parts per million by weight) with respect to the weight of the component (C) and, preferably, in a quantity ranging from 0.01% to 0.3% by weight.

The above transesterification reaction is conveniently carried out at such a pressure as to make the system boil at the pre-selected operating temperature, in order to favour the elimination of the low-boiling products from the reaction mixture: for example, pressure values ranging from 50 mbars and 1030 mbars, preferably from 60 mbars to 800 mbars, are suitable for the purpose.

The reaction is considered as being complete when all the theoretical allyl alcohol deriving from the reaction itself and, optionally, the excess allyl alcohol which may be present when a phthalic ester different from diallyl orthophthalate, diallyl isophthalate or diallyl terephthalate is used as component (B), have been extracted.

Operating under the conditions described above, the reaction times generally range from 0.5 hours to 20 hours, preferably from 1 hour to 10 hours.

After cooling to about 70° C., the above reaction mixture is washed with water to remove the small quantities of residual catalyst and, after the de-mixing and separation of the aqueous phase, the non-reacted diallyl carbonate is eliminated, by heating to a temperature in the order of 130° C., under a decreasing pressure with end-values ranging from 0.1 mbars to 20 mbars, preferably from 0.5 mbars to 2 mbars, obtaining the desired composition as residue.

The composition thus obtained is finally subjected to filtration after optional treatment with activated carbon.

The composition object of the present invention is liquid at room temperature and has viscosity values ranging from 15 cst to 300 cst and density values ranging from 1.1 g/ml to 1.3 g/ml.

The polymerizable liquid composition object of the present invention is a complex mixture which contains diallyl phthalate, bis(allyl carbonate) of component (C) in monomeric and oligomeric form, bis(allyl phthalate) of component (C) in monomeric and oligomeric form, as well as a mixture of mixed oligomeric allyl carbonates and allyl phthalates of component (C), the relative quantities of said constituents of the present composition mainly depending on the pre-selected ratios of the reagents (A), (B) and (C).

The above composition can be transformed into organic glass, by means of radicalic polymerization, using the normal "casting" technique: said organic glass therefore represents a further object of the present invention.

For this purpose, one or more polymerization initiators, soluble in the composition and capable of generating free radicals within a temperature range of 30° C. to 120° C., are added to said composition.

A group of polymerization initiators useful for the purposes of the present invention is the peroxide group.

Preferred examples of peroxides which can be used for the purposes of the present invention are: dicyclohexylperoxydlcarbonate, diisopropylperoxydlcarbonate, dibenzoylperoxide, di(s-butyl-peroxydicarbonate, s-butyl-cyclohexylperoxydicarbonate, etc.

Other peroxides which can be used for the purposes of the present invention are perketals.

Preferred examples of perketals useful for the purposes of the present invention are: 1,1-di-(t-butylperoxy) cyclohexane, 1,1-di-(t-butylperoxy)-3,3,5-tri-methylcyclohexane, 1,1-di-(t-amylperoxy)cyclohexane, 1,1-di(t-butylperoxy)-2-methylcyclohexane, 1,1-di-(t-amylperoxy)-2-methylcyclohexane, etc.

The quantity of initiator used can generally vary within a range of 1 to 6 parts by weight for every 100 parts by weight of the composition object of the present invention.

The composition object of the present invention may optionally contain one or more conventional additives such as, for example, oxidation, light and heat stabilizers, lubricants, dyes, pigments, ultraviolet light absorbers (UV-absorbers), infra-red radiation absorbers (IR-absorbers), and the like, in a total quantity however of not more than 1 part by weight for every 100 parts by weight of the compositions themselves.

Examples of additives which can be used for the purposes of the present invention are: sterically hindered phenols, sterically hindered amines, benzophenones, benzotriazoles, organic phosphates and phosphonites, etc.

The composition object of the present invention containing the polymerization initiator and, optionally, one or more additives selected from those mentioned above, is transformed into the relative organic glass, operating at a temperature ranging from 30° C. to 120° C., with polymerization times which generally vary from 1 hour to 100 hours.

During the polymerization, limited volume contraction phenomena occur and the organic glass thus obtained has a refractive index $(n_D^{20}) \geq 1.53$, good optical and physico-mechanical properties and good dyeability.

Said organic glass is particularly useful in the production of optical articles such as ophthalmic lenses and lenses for optical instruments: these end-products therefore form an additional object of the present invention.

The advantages deriving from the use of the polymerizable liquid composition object of the present invention with respect to the use of compositions of the known art are mainly the following:

first of all, the optical articles obtained have no internal tensions when tested in polarized light;

secondly, the lenses obtained, after immersion in color baths, have homogeneous shades and do not have any defects of a cosmetic nature.

Some illustrative examples are provided for a better understanding of the present invention and for its embodiment, but should not be considered as limiting the scope of the invention in any way.

In the following examples, polymerizable liquid compositions are prepared by reacting, under transesterification conditions, a mixture of diallyl carbonate (A) and a phthalic ester (B) with one or more aliphatic polyols (C).

The polyol (C) used in the examples is indicated each time, as also the possible addition of allyl alcohol.

A peroxide polymerization initiator whose nature and concentration are indicated each time in the following experimental examples, is added to the liquid compositions thus obtained.

The compositions containing the polymerization initiator are transformed, by means of polymerization, into flat plates having a thickness of 3 mm or neutral lenses, using the casting technique. Operating according to this technique, the liquid compositions, containing the polymerization initiator, are poured into the cavity of a mould consisting of two glass elements and having a spacer seal made of plasticized polyvinylchloride, ethylene-vinylacetate (EVA) copolymer, low density polyethylene (LDPE), or another suitable material, compatibly with the operating conditions.

The liquid compositions are then subjected to polymerization by means of thermal treatment in a forced circulation oven, as described hereunder in the experimental examples.

At the end of the above treatment, the moulds are opened and the polymerized products are recovered and maintained at 110° C. for two hours to complete the polymerization reaction and give the end-product dimensional stability.

The following characteristics are determined on the plates thus obtained:

(a) Optical Characteristics

Refractive index $(n_D^{20})$: measured with an Abbe refractometer (ASTM D-542).

Yellow index (YI) (ASTM D-1925) defined as:

$$YI = \frac{100}{Y}(1.277X - 1.06Z)$$

determined with a Macbeth 1500 Plus spectrophotometer.

(b) Physical and Mechanical Characteristics

Density: determined with hydrostatic scales at a temperature of 20° C. (ASTM D-792).

Shrinkage in polymerization calculated with the following formula:

$$\% \text{ shrinkage} = \frac{(\text{polymer density} - \text{monomer density})}{(\text{polymer density})} \times 100$$

Rockwell Hardness (M) measured with a Rockwell durometer (ASTM D-785).

Izod shock resistance without notch (ASTM D-256 modified)

(c) Thermal Characteristics

Deflection temperature under load 1.82 MPa (HDT) (ASTM D-648).

(d) Dyeability

The capacity of the material to absorb a dye on its surface is determined, by immersion ("dip-dyeing") of a neutral lens in an aqueous bath in which the dye BPI Gray is dispersed.

For this purpose, the lens is immersed in said color bath for 10 minutes at a temperature of 80° C. and, after rinsing with demineralized water, the homogeneity of the lens color is determined by sight observation.

From the examples described below, it can be clearly seen that the compositions object of the present invention, as well as having a reduced volume contraction in polymerization, allow the production of organic glass with improved characteristics with respect to the organic glass of the known art:

refractive index higher than that of the organic glass obtained from the polymerization of bis(allyl carbonate) of diethylene glycol;

low yellow index;

high impact strength;

good dyeability and color homogeneity.

EXAMPLE 1

The following products are charged into a three-necked jacketed flask, equipped with a thermometer and magnetic stirrer with an overlying distillation column with 10 perforated plates having a diameter of 30 mm:

| | |
|---|---|
| dimethyl isophthalate (DMIP): | 291 g (1.5 moles); |
| diethylene glycol (DEG): | 106 g (1.0 moles); |
| diallyl carbonate (DAC): | 355 g (2.5 moles); |
| allyl alcohol (AA): | 261 g (4.5 moles) | solution at 20% by weight of sodium methylate in methanol (5.0 ml).

The reaction is carried out for 5 hours at a temperature of 90° C.–110° C. and at a pressure of 700 mbars, the methanol being distilled as it is formed (total 120 ml).

When the distillation of the methanol is complete, the pressure is brought to 200 mbars and the temperature to about 90° C. for 2 hours in order to distill the allyl alcohol (total 237 ml). Finally, the last traces of allyl alcohol are eliminated by gradually bringing the pressure to 50 mbars.

After cooling to about 70° C., the reaction mixture is washed with two portions, each of 500 ml, of distilled water.

The residual diallyl carbonate is distilled at a pressure of about 1 mbar, operating at a temperature increasing to 130° C.: the product obtained is filtered with a 0.45 μm membrane.

470 g of a liquid product having the following characteristics, are obtained:
viscosity (25° C.): 52 cst;
density (20° C.): 1.165 g/ml;
refractive index. ($n_D^{20}$): 1.512;
APHA color: 5.

The above product is a complex mixture containing:
40% by weight of diallyl isophthalate having formula (I);

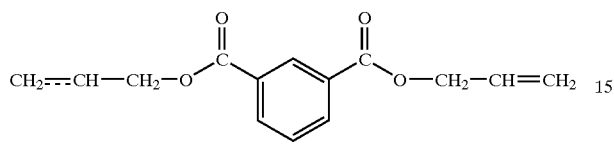

10% by weight of bis(allyl carbonate) of diethylene glycol, monomer and oligomers, having formula (II):

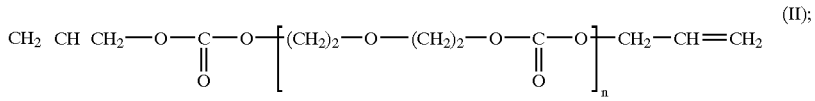

5% by weight of bis(allyl isophthalate) of diethylene glycol, monomer and oligomers, having formula (III):

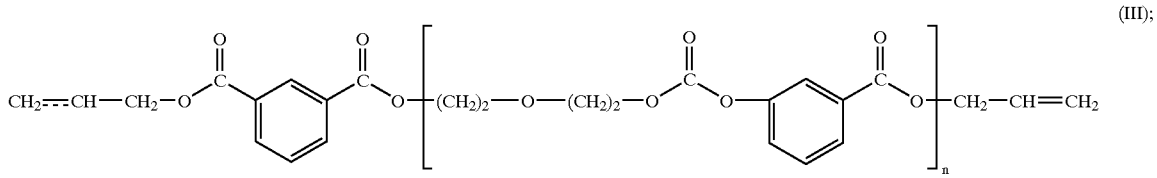

16% by weight of mixed oligomer having formula (IV):

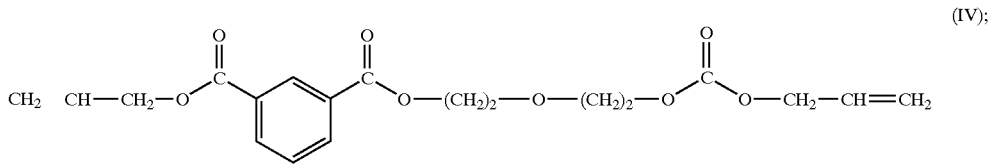

the remaining percentage essentially consisting of higher oligomers of the above mixed oligomer having formula (IV).

The above composition, after the addition of 1,1-di-(t-butylperoxy)-3,3,5-trimethylcyclohexane (3% by weight in the Luperox 231-50 composition of Elf Atochem), is subjected to polymerization in a forced air circulation oven at a temperature of 95° C. for 24 hours. The characteristics indicated in Table 1 are determined on the hardened composition thus obtained.

The yellow index (YI) is determined on a sample having a thickness of 5 mm to which 2-hydroxy-4-methoxybenzophenone (0.1%) has been added.

TABLE 1

| | Composition Example 1 |
|---|---|
| Density (g/ml; 20° C.) | 1.286 |
| Shrinkage (%) | 9.4 |
| Refractive index ($n_D^{20}$) | 1.552 |
| Yellow index (YI) | 1.23 |
| Rockwell hardness (M) | 107 |
| Izod shock resistance without notch (KJ/m$^2$) | 26.7 |
| HDT (° C.) | 61 |
| Dyeability | Lens homogeneously colored |

EXAMPLE 2

Operating according to the procedure described in Example 1, the following compositions 2, 3 and 4 are prepared by reacting diethylene glycol (DEG) with mixtures of diallyl carbonate (DAC) and dimethyl isophthalate (DMIP), or with a mixture of diallyl carbonate (DAC) and dimethyl terephthalate (DMTP), in various molar ratios, in the presence of allyl alcohol (AA), as indicated in Table 2.

Said Table 2 also indicates the viscosity characteristics (cst; 25° C.), density (g/ml; 20° C.), and refractive index ($n_D^{20}$) of the polymerizable liquid compositions obtained.

TABLE 2

| | Composition Nr. | | |
|---|---|---|---|
| | 2 | 3 | 4 |
| DEG (moles) | 1.0 | 1.0 | 1.0 |
| DAC (moles) | 2.5 | 2.0 | 2.5 |
| DMIP (moles) | 1.0 | 1.2 | — |
| DMTP (moles) | — | — | 1.0 |
| AA (moles) | 3.0 | 3.0 | 3.0 |

TABLE 2-continued

|  | Composition Nr. | | |
|---|---|---|---|
|  | 2 | 3 | 4 |
| Viscosity (cst ; 25° C.) | 60 | 92 | 51 |
| Density (g/ml; 20° C.) | 1.168 | 1.176 | 1.169 |
| $n_D^{20}$ | 1.503 | 1.515 | 1.505 |

The above compositions, after the addition of 1,1-di-(t-butylperoxy)-3,3,5-trimethylcyclohexane (3% by weight in the Luperox 231-50 composition), are subjected to polymerization as described in Example 1. The characteristics indicated in Table 3 are determined on the hardened compositions thus obtained.

Also in this case, the yellow index (YI) is determined on a sample having a thickness of 5 mm, to which 2-hydroxy-4-methoxybenzophenone (0.1%) has been added.

TABLE 3

|  | Composition Nr. 2 | Composition Nr. 3 | Composition Nr. 4 |
|---|---|---|---|
| Density (g/ml; 20° C.) | 1.292 | 1.288 | 1.293 |
| Shrinkage (%) | 9.6 | 8.7 | 9.6 |
| Refractive index ($n_D^{20}$) | 1.543 | 1.546 | 1.544 |
| Yellow index (YI) | 1.37 | 1.6 | 1.9 |
| Rockwell hardness (M) | 102 | 105 | 103 |
| Izod shock resistance without notch (kJ/m²) | 35.8 | 32.6 | 19.1 |
| HDT (° C.) | 57 | 60 | 62 |
| Dyeability | Lens homogeneously Colored | Lens homogeneously colored | Lens homogeneously colored |

EXAMPLE 4

Composition 2 is subjected to polymerization in the presence of dicyclohexyl peroxy bicarbonate (4% by weight) as polymerization initiator, operating in a forced air circulation oven with a gradual temperature increase from 35° C. to 80° C. in 20 hours.

The properties indicated in Table 4 are determined on the hardened composition thus obtained.

TABLE 4

| Density (g/ml; 20° C.) | 1.297 |
|---|---|
| Shrinkage (%) | 9.9 |
| Retractive index ($n_D^{20}$) | 1.543 |
| Yellow index (YI) | 3.17 |
| Rockwell hardness (M) | 104 |
| Izod shock resistance without notch (KJ/m²) | 31.8 |
| HDT (° C.) | 58 |
| Dyeability | Lens homogeneously colored |

EXAMPLE 5

Operating according to the procedure described in Example 1, the following compositions 5 and 6 are prepared by reacting diethylene glycol (DEG) and pentaerythritol (PE) with mixtures of diallyl carbonate (DAC) and dimethyl isophthalate (DMIP), in various molar ratios, in the presence of allyl alcohol (AA), as indicated in Table 5.

Table 5 also indicates the viscosity characteristics (cst; 25° C.), density (g/ml; 20° C.), and refractive index ($n_D^{20}$) of the polymerizable liquid compositions obtained.

TABLE 5

|  | Composition Nr. | |
|---|---|---|
|  | 5 | 6 |
| DEG (moles) | 0.95 | 0.95 |
| PE (moles) | 0.05 | 0.05 |
| DAC (moles) | 2.5 | 3.0 |
| AA (moles) | 3.0 | 3.0 |
| Viscosity (cst ; 25° C.) | 82 | 59 |
| Density (g/ml; 20° C.) | 1.177 | 1.172 |
| $n_D^{20}$ | 1.504 | 1.498 |

The above compositions, after the addition of 1,1-di-(t-butylperoxy)-3,3,5-trimethylcyclohexane (3% by weight in the Luperox 231-50 composition), are subjected to polymerization as described in Example 1. The characteristics indicated in Table 6 are determined on the hardened compositions thus obtained.

Also in this case, the yellow index (YI) is determined on a sample having a thickness of 5 mm, to which 2-hydroxy-4-methoxybenzophenone (0.1%) has been added.

TABLE 6

|  | Composition Nr. 5 | Composition Nr. 6 |
|---|---|---|
| Density (g/ml; 20° C.) | 1.294 | 1.295 |
| Shrinkage (%) | 9.1 | 9.5 |
| Refractive index ($n_D^{20}$) | 1.542 | 1.537 |
| Yellow index (YI) | 1.2 | 1.3 |
| Rockwell hardness (M) | 107 | 104 |
| Izod shock resistance without notch (KJ/m²) | 29 | 25.8 |
| HDT (° C.) | 70 | 62 |
| Dyeability | Lens homogeneously colored | Lens homogeneously colored |

What is claimed is:

1. A liquid composition polymerizable, by means of radicalic polymerization, into organic glass, comprising the product obtained from the transesterification of a mixture of diallyl carbonate (A) and a phthalic ester (B), with one or more polyols (C), linear or branched, containing from two to eight carbon atoms in the molecule.

2. The polymerizable liquid composition according to claim 1, wherein the molar ratio (A+B)/C ranges from 2/1 to 7/1 and the molar concentration of (B) in the mixture (A+B) ranges from 10% to 70% with respect to the total of said mixture (A+B).

3. The polymerizable liquid composition according to claim 1 wherein the phthalic esters (B) are ortho, meta or para-phthalates of aliphatic alcohols containing from 1 to 3 carbon atoms in the molecule.

4. The polymerizable liquid composition according to any of the previous claims wherein the phthalic esters (B) are ortho, meta or para-phthalates of aliphatic alcohols containing from 1 to 3 carbon atoms in the molecule.

5. The polymerizable liquid composition according to claim 4, wherein the phthalic esters (B) are: dimethyl orthophthalate, dimethyl isophthalate, dimethyl terephthalate, diethyl orthophthalate, diethyl isophthalate, diethyl terephthalate, dipropyl orthophthalate, dipropyl isophthalate, dipropyl terephthalate, diallyl orthophthalate, diallyl isophthalate, diallyl terephthalate.

6. The polymerizable liquid composition according to claim 1 wherein he polyols (C) are polyols consisting of aliphatic glycols, linear or branched, containing from two to eight carbon atoms in the molecule.

7. The polymerizable liquid composition according to any of the previous claims wherein, when a phthalic ester different from diallyl orthophthalate, diallyl isophthalate or diallyl terephthalate, is used as component (B), allyl alcohol (D) must be added to the reaction mixture in a molar quantity equal to about 1–3 times that of the phthalate (B).

8. The polymerizable liquid composition according to any of the previous claims wherein the polyols (C) are polyols consisting of aliphatic glycols, linear or branched, containing from two to eight carbon atoms in the molecule.

9. The polymerizable liquid composition according to claim 1, wherein the polyols (C) contain also aliphatic polyols, (E) linear or branched, containing from four to twenty carbon atoms and from three to six hydroxyl groups in the molecule.

10. The polymerizable liquid composition according to claim 9, wherein the glycol is diethylene glycol.

11. The polymerizable liquid composition according to any of the claims from 1 to 7, wherein the polyols (C) are aliphatic polyols, linear or branched, containing from four to twenty carbon atoms and from three to six hydroxyl groups in the molecule.

12. The polymerizable liquid composition according to claim 1, wherein the polyols (E) containing from four to twenty carbon atoms and from three to six hydroxyl groups in the molecule can only be used in the reaction mixture combined with polyols consisting of aliphatic glycols, linear or branched, containing from two to eight carbon atoms in the molecule, in a concentration not higher than 200 by weight with respect to the total of the mixture of polyols (C) and (E).

13. A process for the preparation of a polymerizable liquid composition according to claim 1, comprising putting the diallyl carbonate (A), the phthalic ester (B), the polyol (C) and, optionally, the allyl alcohol (D), in contact with each other, operating under transesterification conditions, at a temperature ranging from 80° C. to 160° C., in the presence of a catalyst of the alkaline type.

14. The polymerizable liquid composition according to any of the previous claims, wherein the polyols (C) containing from four to twenty carbon atoms and from three to six hydroxyl groups in the molecule can only be used in the reaction mixture combined with the glycols according to claims 8–10, in a concentration not higher than 20% by weight with respect to the total of the mixture of polyols (C).

15. A process for the preparation of a polymerizable liquid composition according to any of the previous claims, comprising putting the diallyl carbonate (A), the phthalic ester (B), the polyol (C) and, optionally, the allyl alcohol (D), in contact with each other, operating under transesterification conditions, at a temperature ranging from 80° C. to 160° C., in the presence of a catalyst of the alkaline type.

16. The process according to claim 13, wherein the catalyst is used in a quantity equal to at least 1 ppm (parts per million by weight) with respect to the weight of component (C).

17. The process according to claim 13, wherein the transesterification reaction is carried out at a pressure ranging from 50 mbars to 1030 mbars.

18. The process according to claim 13, wherein the reaction times range from 0.5 hours to 20 hours.

19. The polymerizable liquid composition according to claim 1, comprising one or more conventional additives such as oxidation, light and heat stabilizers, lubricants, dyes, pigments, ultraviolet light absorbers (UV-absorbers), infrared radiation absorbers (IR-absorbers), etc., in a total quantity however of not more than 1 part by weight for every 100 parts by weight of the compositions themselves.

20. The process according to any of the claims from 15 to 19, wherein the reaction times range from 0.5 hours to 20 hours.

21. The polymerizable liquid composition according to claim 1, which is transformed into organic glass by radical polymerization using one or more polymerization initiators, operating within a temperature range of 30° C. to 120° C., with polymerization times varying from 1 hour to 100 hours.

22. The polymerizable liquid composition according to claim 21, wherein the additives are: sterically hindered phenols, sterically hindered amines, benzophenones, benzotriazoles, organic phosphites and phosphonites.

23. The polymerizable liquid composition according to any of the previous claims, which is transformed into organic glass by radicalic polymerization using one or more polymerization initiators, operating within a temperature range of 30° C. to 120° C., with polymerization times varying from 1 hour to 100 hours.

24. The polymerizable liquid composition according to claim 23, wherein the polymerization initiators are peroxides.

25. The polymerizable liquid composition according to claim 24, wherein the peroxides are: dicyclohexylperoxydicarbonate, diisopropylperoxydicarbonate, dibenzoylperoxide, di-s-butyl-peroxydicarbonate, s-butyl-cyclohexylperoxydicarbonate.

26. The polymerizable liquid composition according to claim 21, wherein the quantity of initiator used varies within a range of 1 to 6 parts by weight for every 100 parts by weight of the composition itself.

27. Organic glass obtained by radical polymerization of the polymerizable liquid composition according to claim 21.

28. The polymerizable liquid composition according to any of the claims from 23 to 27, wherein the quantity of initiator used varies within a range of 1 to 6 parts by weight for every 100 parts by weight of the composition itself.

* * * * *